United States Patent [19]

Cimino et al.

[11] Patent Number: 5,382,247
[45] Date of Patent: Jan. 17, 1995

[54] TECHNIQUE FOR ELECTROSURGICAL TIPS AND METHOD OF MANUFACTURE AND USE

[75] Inventors: William W. Cimino, Louisville; Michael D. Lontine, Westminster; Michael P. Schollmeyer, Longmont, all of Colo.

[73] Assignee: Valleylab Inc., Boulder, Colo.

[21] Appl. No.: 184,515

[22] Filed: Jan. 21, 1994

[51] Int. Cl.$^6$ .............................................. A61B 17/36
[52] U.S. Cl. .................................. 606/33; 606/28; 606/45; 606/39
[58] Field of Search ........................... 606/45, 27–29, 606/37–44, 46–52

[56] References Cited

U.S. PATENT DOCUMENTS

| | | | |
|---|---|---|---|
| 3,336,916 | 10/1963 | Edlich. | |
| 4,364,390 | 12/1982 | Shaw | 606/29 |
| 4,481,057 | 11/1984 | Beard | 606/28 X |
| 4,785,807 | 11/1988 | Blanch | 606/45 |
| 4,850,353 | 7/1989 | Stasz et al. | 606/45 X |
| 5,100,402 | 3/1992 | Fan | 606/45 X |
| 5,197,962 | 3/1993 | Sansom et al. | 606/45 |

*Primary Examiner*—Peter A. Aschenbrenner

[57] ABSTRACT

An electrosurgical tip for the application of electromagnetic energy in either a monopolar or a bipolar circuit through the tissue and the bodily fluids of an animal or human has a metallic electrically and thermally conductive electrode for connection to an electrosurgical generator proximally and for transmission of the electromagnetic electrosurgical energy to the tissue and the bodily fluids of the animal or human distally. A sheath of heat shrinkable fluorinated polymeric substance is an electrical and thermal insulator held about the electrode for preventing the flow of electromagnetic and thermal energy from the metallic electrically and thermally conductive electrode to the tissue and the bodily fluids. A smooth surface of the sheath contacts the tissue and the bodily fluids and has a low surface free energy. Openings through the sheath extend from the electrode to the surface for permitting the passage of energy. A wall of the sheath is of a thickness adequate to space the electrode from substantially any contact with the tissue and isolate heat due to the arcs. A ceramic substance is an electrical and thermal insulator about the conductive electrode for preventing the energy flow. A method of making the tip includes covering the electrode with the insulator, isolating physically the heat generated due to the passage of energy. A method of using the tip places the surface in close proximity to the tissue and the bodily fluids, transmits the electromagnetic energy through the openings, allows cleaning tissue and bodily fluids from the surface. The use includes first passing energy through openings in a wall of electrical and thermal insulation and application of electromagnetic energy by either a monopolar or a bipolar circuit relative to the tissue and the bodily fluids of an animal or human.

20 Claims, 2 Drawing Sheets

TECHNIQUE FOR ELECTROSURGICAL TIPS AND METHOD OF MANUFACTURE AND USE

FIELD OF THE INVENTION

This relates to electrosurgical tips for the application of electromagnetic energy to tissue of animal and human and more particularly to the cleanability of such tips.

BACKGROUND OF THE DISCLOSURE

Tips for electrosurgical use are subject to high temperature at least whereat the electrosurgical arc emanates during, e.g. fulguration. The heat thus provided causes the proteins in the bodily fluids to coagulate and adhere to the tips.

Coatings have been used to increase the ease of cleanability of the electrosurgical tips. U.S. Pat. No. 4,785,807 has a primer and top coating of Teflon polymer over an etched or abraded stainless steel tip. The coating is thin and during application of electromagnetic energy it is said that there is capacitive coupling to allow passage of power to the tissue being treated. Thus, the Teflon polymer surface should remain largely intact and so the cleanability of the tip is good.

U.S. Pat. No. 4,492,231 discusses temperature, tip conductivity and sticking of desiccated blood in a bipolar forceps.

U.S. Pat. Nos. 4,232,676 and 4,314,559 assigned to Corning Glass Works, disclose tips that with areas for electrosurgery and other areas which do not conduct high frequency power. The '676 patent has bipolar electrodes on the same tip so that power passing therebetween will cauterize bleeders. The '559 patent is an electrically conductive tip with a rough surface finish filled with Teflon polymer to provide non-stick properties. Thus, portions of the tip are not covered and form an electrical connection between surgical tip and the tissue. The Teflon polymer only fills interstices, inclusions and the like at the surface, thus providing non-stick areas on the cutting or coagulating instrument. The '559 patent has a surface which provides areas of Teflon polymer and raw metal and so recognizes the conductive nature of the tip and permits energy flow without the need to overcome the electrical insulation of the coating. Specifically, interstices along the surface of the metal tip are filled with primer and a top coat of Teflon polymer. The surface is thus partly conductive metal and partly cleanable Teflon polymer.

Australian patent 637755 has a conductive shaft with insulation providing both electrical and thermal insulation and abrasion-resistance along the shaft between its ends, and is e.g., provided by a shrink fitted plastic tube. The purpose of this is strictly an electrical insulator with no appreciation of blade anti-coagulation.

No electrosurgical tips exist wherein a relatively thick sheath of fluorinated polymer having areas open to expose metallic conductor therewithin and provide an effective thermal and electrical barrier are known in the prior patents. It has been found that the cleanability of the electrosurgical tips is a function of surface temperature and surface free energy. The ability to provide electrosurgical energy while minimizing heat transfer to the tissue and significantly reducing adherence to the tip is presently not appreciated in the prior patents.

SUMMARY OF THE INVENTION

An electrosurgical tip for the application of electromagnetic energy in either a monopolar or a bipolar circuit through the tissue and the bodily fluids of an animal or human preferably has an electrically conductive electrode for connection to a source of electromagnetic electrosurgical energy and for transmission of the energy. An electrical and thermal insulator is preferably held about the conductive electrode for preventing the flow of electromagnetic and thermal energy from the electrically conductive electrode to the tissue and the bodily fluids. A surface of the electrical and thermal insulator for contact with the tissue and the bodily fluids most preferably has a low surface free energy. The surface is a fluorinated polymer.

Openings through the electrical and thermal insulator may be provided to extend from the electrically conductive electrode to the surface for the passage of energy from the electrode to the tissue and the bodily fluids. A wall of the electrical and thermal insulator between the surface of the electrical and thermal insulator and the electrically conductive electrode most preferably has a thickness ample to space the electrode from substantially any contact with the tissue and to physically isolate heat generated in the conductive electrode due to passage energy through the openings.

The electrical and thermal insulator is in a preferred embodiment a heat shrinkable polymeric sheath. The electrical and thermal insulator may alternatively be a ceramic substance with the surface thereof sheathed or treated to reduce its surface free energy. The wall of the insulator may be a porous substance having an open cellular configuration allowing passage of electromagnetic energy from the electrode to the tissue and the bodily fluids and preventing the flow of thermal energy so there is a thermal gradient between the electrically conductive electrode and the surface. The electrically conductive electrode is at least in part metallic having electrical and thermal conductivity and may perhaps be selected from the group consisting of copper, gold, silver, aluminum, ferrous alloys and alloys thereof.

The surface is in an alternative embodiment a material different from that of the sheath. The surface may have a lower surface free energy than the wall. The surface might have a coating having a low surface free energy. The coating might be lubricous. The ceramic substance may act as an electrical and thermal insulator about the conductive electrode for preventing the flow of electromagnetic and thermal energy from the conductive electrode to the tissue and the bodily fluids. The ceramic substance is preferably of a thickness ample to space the conductive electrode from substantially any contact with the tissue and to physically isolate heat generated in the conductive electrode due to flow of electromagnetic energy through the electrically conductive electrode.

A method of making an electrosurgical tip for the application of electromagnetic energy in either a monopolar or a bipolar circuit through the tissue and the bodily fluids of an animal or human has steps. Connecting an electrically conductive electrode to a source of electromagnetic electrosurgical energy may be a step. Covering the electrically conductive electrode with an electrical and thermal insulator may be a step. Providing openings in the electrical and thermal insulator, the openings extending therethrough from the electrically conductive electrode for permitting passage of electromagnetic electrosurgical energy from the electrically conductive electrode to the tissue and the bodily fluids may be a step. Providing the surface with a low surface free energy may be a step. Extending the openings through the surface may be a step. Providing a wall in the electrical and thermal insulator between the surface and the electrically conductive electrode may be a step. Making the wall of a thickness ample to space the conductive electrode from substantially any contact with the tissue of the animal or human may be a step. Isolating physically the heat generated due to the passage of energy from the electrically conductive electrode through the openings to the tissue and the bodily fluids of the animal or human may be a step.

The method of making may include the step of covering performed by heat shrinking a polymeric tube place over the electrically conductive electrode. The method of making might have the step of providing the openings performed before or after heat shrinking the tube. A method of using an electrosurgical tip that is electrically and thermally insulated but has openings for passage of and the application of electromagnetic energy in either a monopolar or a bipolar circuit through the tissue and the bodily fluids of an animal or human has steps. Placing in close proximity to the tissue and the bodily fluids of the animal or human a surface of the electrical and thermal insulator may be a step. Transmitting the electromagnetic energy through the openings to the tissue and the bodily fluids of the animal or human may be a step. Cleaning tissue and bodily fluids from the surface may be a step. Transmitting the electromagnetic energy includes first passing it through openings in a wall of electrical and thermal insulation may be a step. Application of electromagnetic energy either by monopolar or bipolar circuitry relative to the tissue and the bodily fluids of an animal or human is a step.

DETAILED DESCRIPTION OF THE INVENTION

Figure 1:
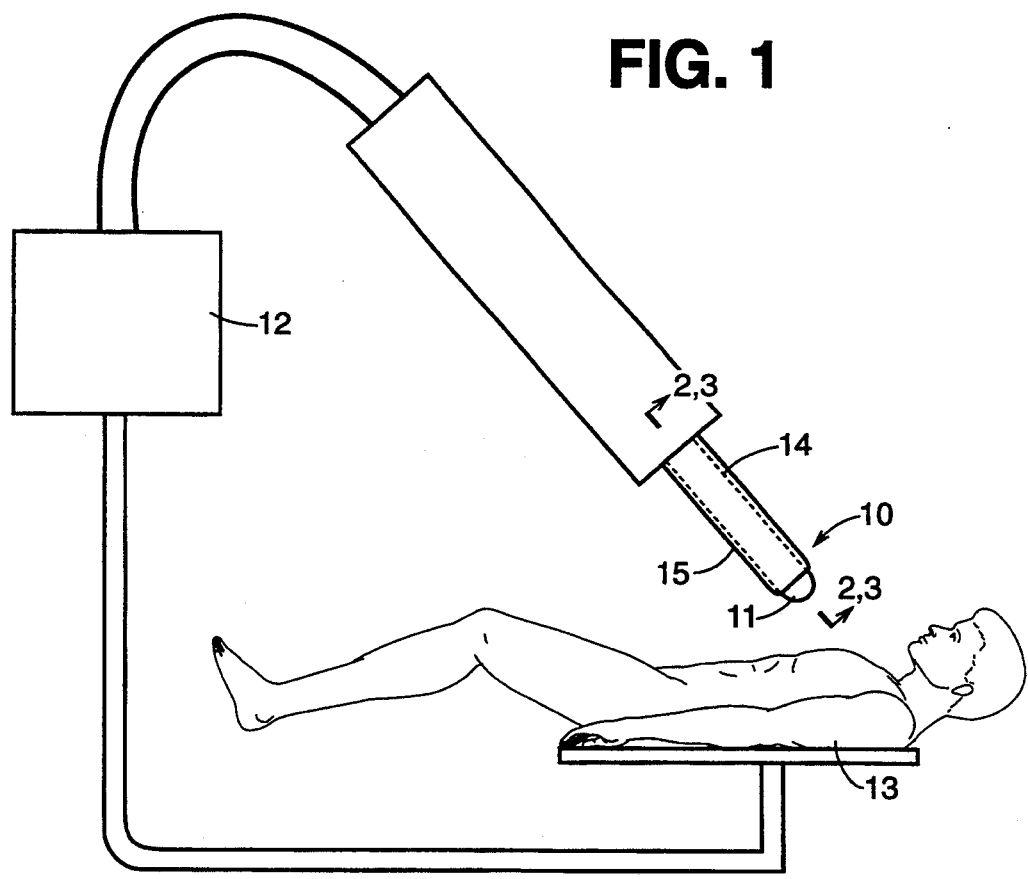
FIG. 1 is an electrosurgical tip for the application of electromagnetic energy in either a monopolar or a bipolar circuit shown schematically and in perspective.
Figure 2:
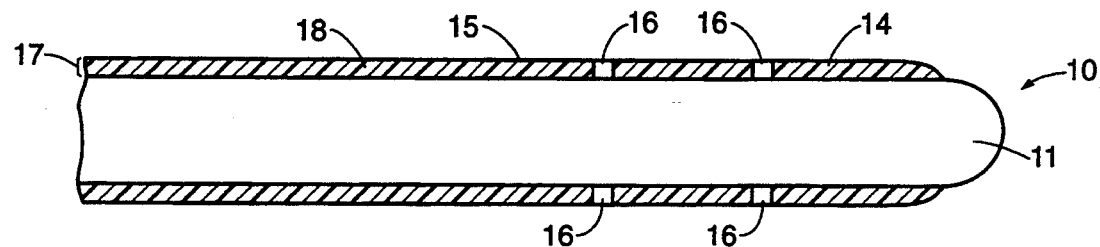
FIG. 2 is a side view in cross section as taken along lines 2—2 of FIG. 1 of the preferred embodiment of an electrosurgical tip.
Figure 4:
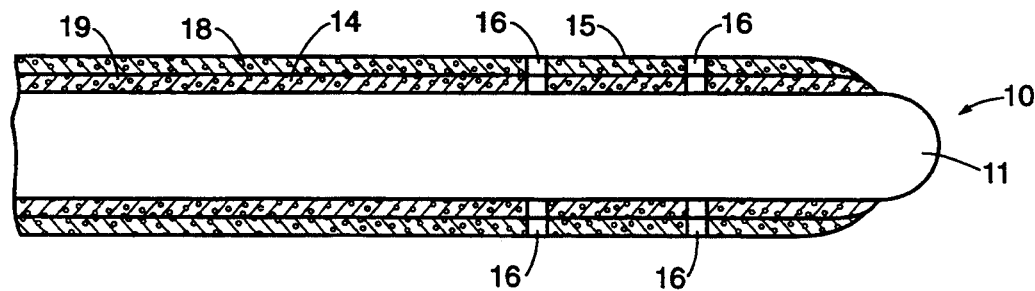
FIG. 4 is a side view in cross section of an electrosurgical tip showing schematically the coating or layer having a low surface energy and the porous material permitting the passage of electrically conductive energy.

In FIG. 1 is an electrosurgical tip 10 for the application of electromagnetic energy in either a monopolar or a bipolar circuit and is shown schematically in perspective and in the alternative. In FIG. 2, a side view in cross section as taken along lines 2—2 of FIG. 1 of the preferred embodiment, the electrosurgical tip is disclosed. FIG. 4 is another side view in cross section of the electrosurgical tip which shows schematically a coating or layer having a low surface energy and a porous material permitting the passage of electrically conductive energy. An electrically conductive electrode 11 connects to a source of electromagnetic electrosurgical energy 12 for transmission of the electromagnetic electrosurgical energy to the tissue and the bodily fluids of the animal or human 13. An electrical and thermal insulator 14 is held about the electrically conductive electrode 11 for preventing the flow of electromagnetic and thermal energy from the electrically conductive electrode 11 to the tissue and the bodily fluids. A surface 15 of the electrical and thermal insulator 14 contacts the tissue and the bodily fluids of the animal or human 13. The surface having a low surface free energy. Openings 16 through the electrical and thermal insulator 14 extend from the electrically conductive electrode 11 to the surface 15 for the passage of electromagnetic electrosurgical energy from the electrically conductive electrode 11 to the tissue and the bodily fluids.

A wall 17 of the electrical and thermal insulator 14 is between the surface 15 of the electrical and thermal insulator 14 and the electrically conductive electrode 11. The wall 17 is of a thickness ample to space the conductive electrode 11 from substantially any contact with the tissue of the animal or human 13 and to physically isolate heat generated in the conductive electrode due to the passage of energy from the electrically conductive electrode 11 through the openings 16 to the tissue and the bodily fluids of the animal or human 13. Thickness of fluorocarbon polymer in the range of 3 to 10 thousanths of an inch are preferred.

Figure 3:
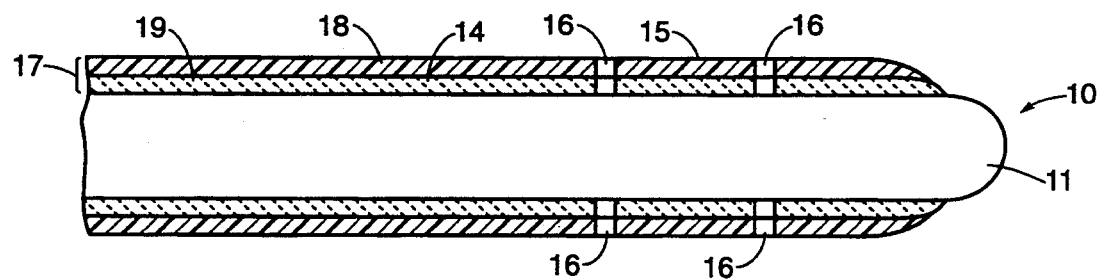
FIG. 3 is a side view in cross section as taken along lines 3—3 of FIG. 1 of the alternate embodiment of an electrosurgical tip.

In FIG. 3, a side view in cross section as taken along lines 3—3 of FIG. 1, the alternate embodiment of the electrosurgical tip 10 is revealed. Specifically, the electrical and thermal insulator 14 may be a sheath 18 of a polymeric substance (FIG. 2) or a ceramic substance 19 (FIG. 3). The surface 15 of the sheath 18 may be treated to reduce its surface free energy. The wall 17 of the sheath 18 may be in one embodiment a porous substance having an open cellular configuration, as shown in FIG. 4, allowing passage of electromagnetic energy from the electrically conductive electrode 11 to the tissue and the bodily fluids while preventing the flow of thermal energy and/or electromagnetic energy so there is a thermal gradient between the electrically conductive electrode 11 and the surface 15.

The electrically conductive electrode 11 is at least in part metallic and preferably medical grade stainless steel, having electrical and thermal conductivity or could be selected from the group consisting of copper, gold, silver, aluminum, ferrous alloys and alloys thereof. The surface 15 is preferably a fluorinated polymer, e.g. Teflon by DuPont. The surface 15 may be a material different from that of the sheath 18 to minimize its surface free energy. The surface 15 may have an extra coating (not shown) having a low surface free energy or to reduce the surface free energy of the surface 15. The coating may be lubricous, i.e. lanolin, silicone, etc. the surface 15 of the sheath 18 if ceramic, porous or such that it has high surface free energy is preferrably coated with a material of low surface free energy, e.g. a flourocarbon or silicone and in that instance the coating thickness can be thin in the range of $\frac{1}{2}$ to 3 thousanths of an inch since the thermal barrier is the sheath 18.

The sheath 18 is most preferably of a heat shrinkable polymeric substance, as an electrical and thermal insulator, slid over the electrically conductive electrode and held thereabout for preventing the flow of electromagnetic and thermal energy from the electrically conductive electrode to the tissue and the bodily fluids. The sheath 18 of a heat shrinkable polymer may be applied over the ceramic substance 19 as in FIG. 3 for surrounding and for contact with the tissue and the bodily fluids of the animal or human 13. The openings 16 in that alternate embodiment can be through the sheath 18 and the ceramic substance 19.

A method of making the electrosurgical tip 10 for the application of electromagnetic energy in either a monopolar or a bipolar circuit through the tissue and the bodily fluids of the animal or human 13 has steps. Connecting the electrically conductive electrode 11 to the source of electromagnetic electrosurgical energy 12 is a step in making the electrosurgical tip 10. Covering the electrically conductive electrode 11 with the electrical and thermal insulator 14 is another step in the making of the electrosurgical tip 10. Providing openings 16 in the electrical and thermal insulator 14 so that the openings 16 extend therethrough from the electrically conductive electrode 11 for permitting passage of electromagnetic electrosurgical energy from the electrically conductive electrode 11 to the tissue and the bodily fluids is a further step in the making.

Then the step of providing the surface 15 with a low surface free energy is performed. Extending the openings 16 through the surface 15 allows the passage of electromagnetic energy. Providing the wall 17 in the electrical and thermal insulator between the surface 15 and the electrically conductive electrode 11 is a step. Making the wall 17 of a thickness ample to space the electrically conductive electrode 11 from substantially any contact with the tissue of the animal or human 13 is the step that prevents thermal energy transmission. Isolating physically the heat generated in the conductive electrode due to the passage of energy from the electrically conductive electrode 11 through the openings 16 to the tissue and the bodily fluids of the animal or human 13 is another step. The step of covering is preferably performed by heat shrinking a polymeric tube placed over the electrically conductive electrode 11. The step of providing the openings 16 may be performed before heat shrinking the tube. The step of providing the openings 16 may alternately be performed after heat shrinking the tube.

A method of using the electrosurgical tip 10 that is electrically and thermally insulated but has openings 16 for passage of and the application of electromagnetic energy in either a monopolar or a bipolar circuit through the tissue and the bodily fluids of the animal or human 13 has steps. Placing in close proximity to the tissue and the bodily fluids of the animal or human 13 the surface 15 of the electrical and thermal insulator 14 is a step. Transmitting the electromagnetic energy through the openings 16 to the tissue and the bodily fluids of the animal or human 13 is a further step. Cleaning tissue and bodily fluids from the surface 15 is another step. The step of transmitting the electromagnetic energy includes first passing it through openings 16 in the wall 17 of electrical and thermal insulation 14. The step of application of electromagnetic energy is either by monopolar or bipolar circuitry relative to the tissue and the bodily fluids of the animal or human 13. The claims which follow seek to protect the technique and apparatus for providing an electrosurgical tip that significantly reduces the adherence of coagulated tissue protein by minimizing surface temperature with a low surface free energy conductive tip.

What is claimed is:

1. An electrosurgical tip for the application of electromagnetic energy in either a monopolar or a bipolar circuit through the tissue and the bodily fluids of an animal or human comprising:
   an electrically conductive electrode for connection to a source of electromagnetic electrosurgical energy and for transmission of the electromagnetic electrosurgical energy to the tissue and the bodily fluids of the animal or human;
   an electrical and thermal insulator held about the electrically conductive electrode for preventing the flow of electromagnetic and thermal energy from the electrically conductive electrode to the tissue and the bodily fluids;
   a surface of the electrical and thermal insulator for contact with the tissue and the bodily fluids of the animal or human, the surface having a low surface free energy;
   openings through the electrical and thermal insulator, the openings extending from the electrically conductive electrode to the surface for the passage of electromagnetic electrosurgical energy from the electrically conductive electrode to the tissue and the bodily fluids, and
   a wall of the electrical and thermal insulator traversing between the surface of the electrical and thermal insulator and the electrically conductive electrode recessed in the openings, the wall of a thickness about the openings and ample to space the electrically conductive electrode from substantially any direct contact with the tissue of the animal or human and to physically isolate heat generated in the electrically conductive electrode due to the passage of energy from the electrically conductive electrode through the openings to the tissue and the bodily fluids of the animal or human.

2. The electrosurgical tip for the application of electromagnetic energy to the tissue or bodily fluids of an animal or human of claim 1 wherein the electrical and thermal insulator is a sheath.

3. The electrosurgical tip for the application of electromagnetic energy to the tissue or bodily fluids of an animal or human of claim 2 wherein the sheath is a polymeric substance.

4. The electrosurgical tip for the application of electromagnetic energy to the tissue and the bodily fluids of an animal or human of claim 2 wherein the sheath is a ceramic substance and the surface thereof is treated to reduce its surface free energy.

5. The electrosurgical tip for the application of electromagnetic energy to the tissue and the bodily fluids of an animal or human of claim 3 wherein the wall of the sheath is a porous substance having an open cellular configuration allowing passage of electromagnetic energy from the electrically conductive electrode to the tissue and the bodily fluids and preventing the flow of thermal energy so there is a thermal gradient between the electrically conductive electrode and the surface.

6. The electrosurgical tip for the application of electromagnetic energy to the tissue and the bodily fluids of an animal or human of claim 4 wherein the wall of the sheath is a porous substance having an open cellular configuration allowing passage of electromagnetic energy from the electrically conductive electrode to the tissue and the bodily fluids and preventing the flow of thermal energy so there is a thermal gradient between the electrically conductive electrode and the surface.

7. The electrosurgical tip for the application of electromagnetic energy to the tissue and the bodily fluids of an animal or human of claim 1 wherein the electrically conductive electrode is at least in part metallic having electrical and thermal conductivity and is selected from the group consisting of copper, gold, silver, aluminum, ferrous alloys and alloys thereof.

8. The electrosurgical tip for the application of electromagnetic energy to the tissue and the bodily fluids of an animal or human of claim 1 wherein the surface is a fluorinated polymer.

9. The electrosurgical tip for the application of electromagnetic energy to the tissue and the bodily fluids of an animal or human of claim 1 wherein the surface is a material different from that of the sheath, the surface having a low surface free energy.

10. The electrosurgical tip for the application of electromagnetic energy to the tissue and the bodily fluids of an animal or human of claim 1 wherein the surface has a coating having a low surface free energy.

11. The electrosurgical tip for the application of electromagnetic energy to the tissue and the bodily fluids of an animal or human of claim 1 wherein the coating is lubricous.

12. An electrosurgical tip for the application of electromagnetic energy in either a monopolar or a bipolar circuit through the tissue and the bodily fluids of an animal or human comprising:

an electrically conductive electrode for connection to a source of electromagnetic electrosurgical energy and for transmission of the electromagnetic electrosurgical energy to the tissue and the bodily fluids of the animal or human;

a sheath of heat shrinkable polymeric substance as an electrical and thermal insulator held about the electrically conductive electrode for preventing the flow of electromagnetic and thermal energy from the electrically conductive electrode to the tissue and the bodily fluids;

a surface of the sheath for contact with the tissue and the bodily fluids of the animal or human, the surface having a low surface free energy for contact with the tissue and the bodily fluids;

openings through the sheath, the openings extending from the electrically conductive electrode to the surface for the passage of electromagnetic electrosurgical energy from the electrically conductive electrode to the tissue and the bodily fluids, and a wall of the sheath between the surface and the electrically conductive electrode, the wall of a thickness about the openings and ample to space the electrically conductive electrode recessed in the openings from substantially any direct contact with the tissue of the animal or human and to physically isolate heat generated in the electrically conductive electrode due to the passage of energy from the electrically conductive electrode through the openings to the tissue and the bodily fluids of the animal or human.

13. An electrosurgical tip for the application of electromagnetic energy in either a monopolar or a bipolar circuit through the tissue and the bodily fluids of an animal or human comprising:

an electrically conductive electrode for connection to a source of electromagnetic electrosurgical energy and for transmission of the electromagnetic electrosurgical energy to the tissue and the bodily fluids of the animal or human;

a ceramic substance as an electrical and thermal insulator about the electrically conductive electrode for preventing the flow of electromagnetic and thermal energy from the electrically conductive electrode to the tissue and the bodily fluids, the ceramic substance of a thickness about the openings and ample to space the electrically conductive electrode recessed in the openings from substantially any direct contact with the tissue of the animal or human and to physically isolate heat generated in the electrically conductive electrode due to flow of electromagnetic energy through the electrically conductive electrode;

a sheath of a heat shrinkable polymer for surrounding the ceramic substance and for contact with the tissue and the bodily fluids of the animal or human;

a surface on the sheath having a low surface free energy for contact with the tissue and the bodily fluids;

openings through the sheath and the ceramic substance, the openings extending from the electrically conductive electrode through the surface for the passage of electromagnetic electrosurgical energy from the electrically conductive electrode to the tissue and the bodily fluids.

14. A method of making an electrosurgical tip for the application of electromagnetic energy in either a monopolar or a bipolar circuit through the tissue and the bodily fluids of an animal or human having the steps of:

connecting an electrically conductive electrode to a source of electromagnetic electrosurgical energy;

covering the electrically conductive electrode with an electrical and thermal insulator having a surface;

providing openings in the electrical and thermal insulator, the openings extending therethrough from the electrically conductive electrode for permitting passage of electromagnetic electrosurgical energy from the electrically conductive electrode to the tissue and the bodily fluids;

providing the surface with a low surface free energy;

extending the openings through the surface;

providing a wall in the electrical and thermal insulator between the surface and the electrically conductive electrode;

making the wall of a thickness about the openings and ample to space the electrically conductive electrode recessed in the openings from substantially any direct contact with the tissue and of the animal or human, and isolating physically the heat generated in the electrically conductive electrode due to the passage of energy from the electrically conductive electrode through the openings to the tissue and the bodily fluids of the animal or human.

15. The method of making an electrosurgical tip for the application of electromagnetic energy of claim 14 wherein the step of covering is performed by heat shrinking a polymeric tube place over the electrically conductive electrode.

16. The method of making an electrosurgical tip for the application of electromagnetic energy of claim 15 wherein the step of providing the openings is performed before heat shrinking the tube.

17. The method of making an electrosurgical tip for the application of electromagnetic energy of claim 15 wherein the step of providing the openings is performed after heat shrinking the tube.

18. A method of using an electrosurgical tip that is electrically and thermally insulated but has openings for passage of and the application of electromagnetic energy in either a monopolar or a bipolar circuit through the tissue and the bodily fluids of an animal or human having the steps of:

placing in close proximity to the tissue and the bodily fluids of the animal or human a surface of the electrical and thermal insulator;

transmitting the electromagnetic electrosurgical energy through the openings to the tissue and the bodily fluids of the animal or human;

delivering electromagnetic electrosurgical energy through openings in a wall of the electrical and thermal insulation from the electrically conductive electrode recessed in the openings to a surface of the wall;

spacing the electrically conductive electrode recessed in the openings from substantially any direct contact with the tissue of the animal or human with the wall of a thickness about the openings ample to provide thermal insulation, and cleaning tissue and bodily fluids from the surface.

19. The method of using the electrosurgical tip of claim 18 wherein the step of application of electromagnetic energy is either by monopolar or bipolar circuitry relative to the tissue and the bodily fluids of an animal or human.

20. An electrosurgical tip for the application of electromagnetic energy in either a monopolar or a bipolar circuit through the tissue and the bodily fluids of an animal or human comprising:

a metallic electrically and thermally conductive electrode for connection to an electrosurgical generator proximally and for transmission of the electromagnetic electrosurgical energy to the tissue and the bodily fluids of the animal or human distally;

a sheath of heat shrinkable fluorinated polymeric substance as an electrical and thermal insulator held about the metallic electrically and thermally conductive electrode for preventing the flow of electromagnetic and thermal energy from the metallic electrically and thermally conductive electrode to the tissue and the bodily fluids;

a smooth surface of the sheath for contact with the tissue and the bodily fluids of the animal or human, the surface having a low surface free energy;

openings through the sheath, the openings extending from the metallic electrically and thermally conductive electrode to the smooth surface for permitting the passage of electromagnetic electrosurgical energy in the form of arcs from the metallic electrically and thermally conductive electrode to the tissue and the bodily fluids, and a wall of the sheath between the smooth surface and the metallic electrically and thermally conductive electrode, the wall of a thickness about the openings and adequate to space the metallic electrically and thermally conductive electrode recessed in the openings from substantially any direct contact with the tissue and the bodily fluids of the animal or human and to physically isolate heat generated in the electrically conductive electrode due to the emission of arcs from the metallic electrically and thermally conductive electrode through the openings to the tissue and the bodily fluids of the animal or human.

* * * * *